United States Patent
Park et al.

(10) Patent No.: US 7,650,189 B1
(45) Date of Patent: Jan. 19, 2010

(54) TECHNIQUES TO MAINTAIN OR ALTER UPPER AIRWAY PATENCY

(75) Inventors: Euljoon Park, Valencia, CA (US);
Michael Benser, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 415 days.

(21) Appl. No.: 11/446,179

(22) Filed: Jun. 2, 2006

(51) Int. Cl.
 *A61N 1/00* (2006.01)
(52) U.S. Cl. ........................................ 607/42
(58) Field of Classification Search ............ 607/42
 See application file for complete search history.

(56) References Cited

U.S. PATENT DOCUMENTS

| | | | |
|---|---|---|---|
| 4,712,555 A | 12/1987 | Thornander et al. | 128/419 PG |
| 4,788,980 A | 12/1988 | Mann et al. | 128/419 PG |
| 4,830,008 A * | 5/1989 | Meer | 607/42 |
| 4,940,052 A | 7/1990 | Mann et al. | 128/419 PG |
| 4,944,298 A | 7/1990 | Sholder | 128/419 PG |
| 5,411,531 A * | 5/1995 | Hill et al. | 607/14 |
| 5,466,254 A | 11/1995 | Helland | 607/123 |
| 5,476,483 A | 12/1995 | Bornzin et al. | 607/17 |
| 5,549,655 A * | 8/1996 | Erickson | 607/42 |
| 5,591,216 A | 1/1997 | Testerman et al. | 607/42 |
| 6,006,134 A * | 12/1999 | Hill et al. | 607/9 |
| 6,314,323 B1 | 11/2001 | Ekwall | 607/23 |
| 6,587,725 B1 * | 7/2003 | Durand et al. | 607/42 |
| 2005/0085874 A1 | 4/2005 | Davis et al. | 607/66 |
| 2005/0119711 A1 * | 6/2005 | Cho et al. | 607/42 |

FOREIGN PATENT DOCUMENTS

| | | |
|---|---|---|
| EP | 0 702 977 A2 | 3/1996 |
| EP | 0 743 076 A1 | 11/1996 |
| EP | 0 702 977 A3 | 3/1997 |
| EP | 0 706 808 B1 | 5/2002 |
| EP | 0 702 978 B1 | 8/2002 |
| EP | 0 702 977 B1 | 3/2003 |
| EP | 1 306 104 A2 | 5/2003 |
| EP | 0 743 076 B1 | 7/2003 |
| EP | 1 306 104 A3 | 8/2004 |
| EP | 1 524 007 A1 | 4/2005 |
| WO | WO 00/06249 A2 | 2/2000 |
| WO | WO 00/06249 A3 | 2/2000 |

OTHER PUBLICATIONS

Khalil Salame et al., "*Surgical Anatomy of the Cervical Segment of the Hypoglossal Nerve*", Clin. Anat., 2006; vol. 19, pp. 37-43.
P. Saraswathi, "*Communication Between the Vagus and Hypoglossal Nerves*", Eur J Anat., 2003; vol. 7, No. 3, pp. 131-134.
Tetsuo Shioi, MD, PhD, et al., "*Rapamycin Attenuates Load-Induced Cardiac Hypertrophy in Mice*", Circulation, Apr. 2003; vol. 107, No. 12, pp. 1664-1670.
Virend K. Somers, "*Sympathetic Neural Mechanisms in Obstructive Sleep Apnea*", J. Clin. Invest., 1995; vol. 96, pp. 1897-1904.

* cited by examiner

Primary Examiner—George Manuel

(57) ABSTRACT

An exemplary method includes calling for delivery of energy to one or more electrodes positionable proximate to an autonomic pathway to alter tone of the genioglossus muscle. Such a method may maintain or alter upper airway patency and, in turn, prevent or alleviate obstructive apnea. Other exemplary methods, devices, systems, etc., are also disclosed.

22 Claims, 8 Drawing Sheets

TECHNIQUES TO MAINTAIN OR ALTER UPPER AIRWAY PATENCY

FIELD OF THE INVENTION

Subject matter presented herein generally relates to techniques to maintain or alter upper airway patency to thereby prevent or alleviate obstructive apnea.

BACKGROUND

There is growing evidence that apnea plays a role in the progression of congestive heart failure (CHF) and that various forms of treatment can lead to improved outcomes. Obstructive sleep apnea (OSA) and central sleep apnea (CSA) occur quite commonly patients with CHF. In general, cardiac output decreases during apnea. For example, in OSA, repetitive pharyngeal collapses have been demonstrated to lower cardiac output by increasing the left ventricular transmural pressure. During airway collapse, intrathoracic pressure decreases substantially and thereby alters ventricular filling, which, in turn, worsens cardiac output.

As apnea has detrimental consequences, a need exists for new or improved techniques to prevent or treat apnea. As described herein, various exemplary techniques maintain or alter upper airway patency to prevent airway collapse. Such techniques are optionally implemented in conjunction with one or more other therapies.

SUMMARY

An exemplary method includes calling for delivery of energy to one or more electrodes positionable proximate to an autonomic pathway to alter tone of the geniglossus muscle. Such a method may maintain or alter upper airway patency and, in turn, prevent or alleviate obstructive apnea. Other exemplary methods, devices, systems, etc., are also disclosed.

In general, the various methods, devices, systems, etc., described herein, and equivalents thereof, are optionally suitable for use in a variety of pacing therapies, other cardiac related therapies, etc.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Various exemplary methods, devices, systems, etc., described herein pertain to upper airway patency. In particular, sensing and/or stimulation are used to maintain or alter upper airway patency, especially in instances where a patient is at risk of or experiencing obstructive apnea. An exemplary implantable device is described below followed by a description of anatomy related to the upper airway. Various exemplary methods are presented along with an exemplary device having one or more electrodes positionable proximate to the hypoglossal nerve for purposes of, for example, maintaining and/or altering upper airway patency.

Exemplary Stimulation Device

Figure 1:
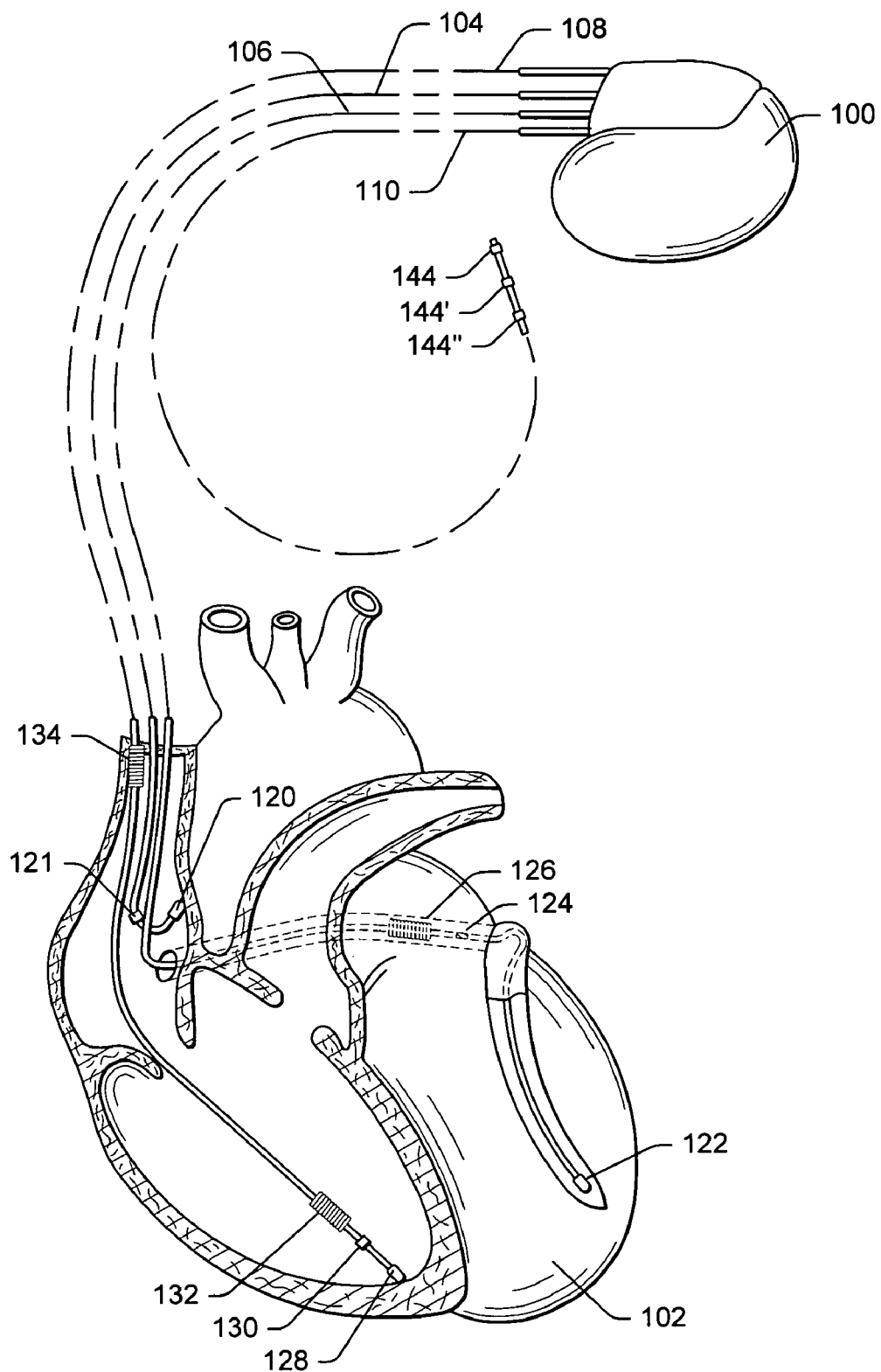
FIG. 1 is a simplified diagram illustrating an exemplary implantable stimulation device in electrical communication with three leads implanted into a patient's heart and at least one other lead positionable proximate to an upper airway muscle or nerve. An exemplary device may have more leads or fewer leads.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for stimulation of autonomic nerves, non-myocardial tissue, other nerves, etc. For example, this lead may be positioned in and/or near a patient's heart or near an autonomic nerve within a patient's body and remote from the heart. Various examples described herein include positioning a lead proximate to the hypoglossal nerve for purposes of sensing and/or stimulating this nerve or a connection to this nerve.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
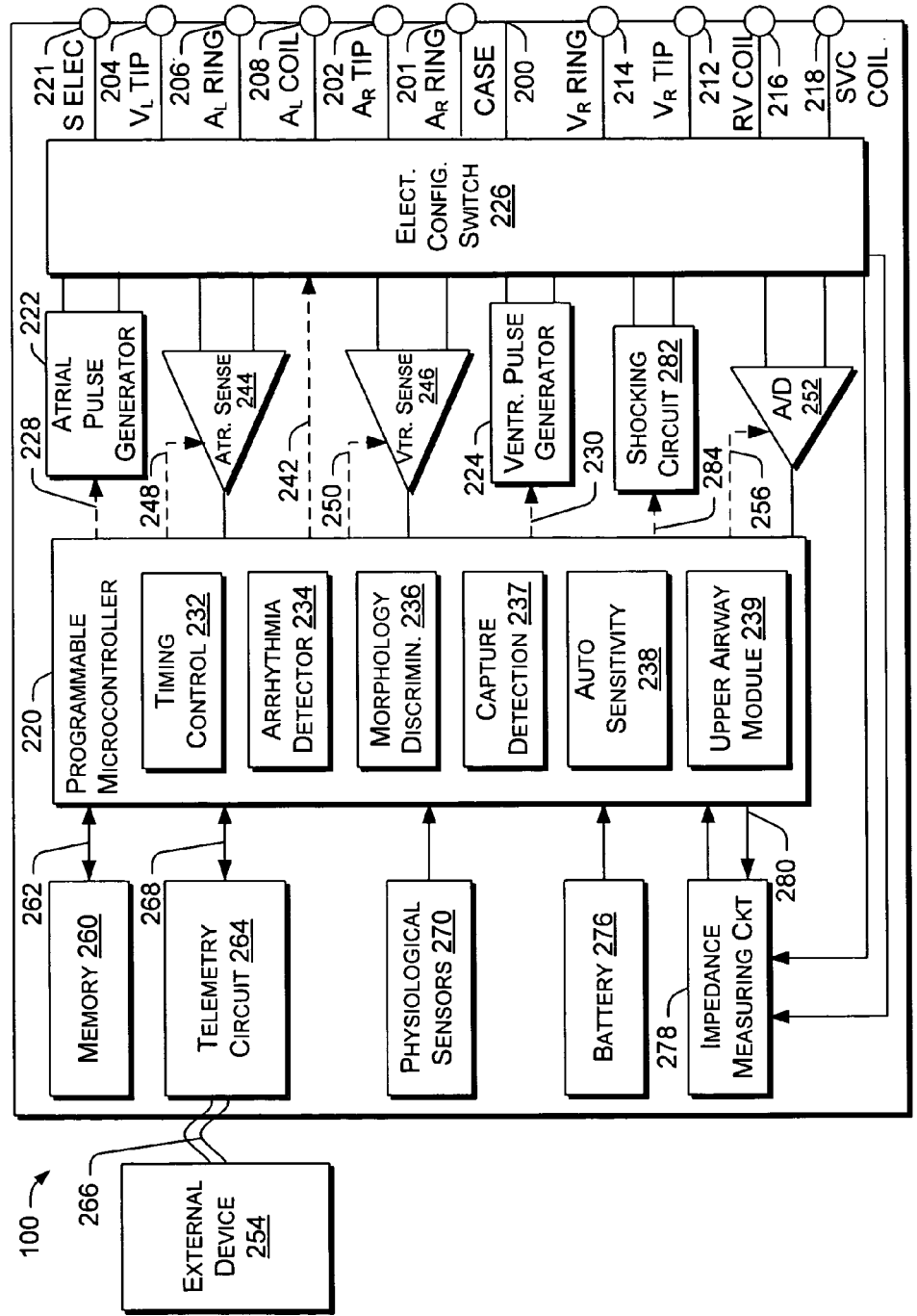
FIG. 2 is a functional block diagram of an exemplary implantable stimulation device illustrating basic elements that are configured to provide cardioversion, defibrillation, pacing stimulation or other tissue or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology discrimination module 236, a capture detection module 237, a auto sensitivity module 238, an upper airway module 239 and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The upper airway module 239 may perform a variety of tasks related to, for example, upper airway patency. This component can be utilized by the stimulation device 100 in determining therapy in response to respiration, other information, a schedule, etc. The upper airway module 239 may be implemented in hardware as part of the microcontroller 220, or as software/firmware instructions programmed into the device and executed on the microcontroller 220 during certain modes of operation. The upper airway module 239 may optionally implement various exemplary methods described herein. The upper airway module 239 may interact with the physiological sensors 270, the impedance measuring circuit 278 and optionally other modules. One or more of the physiological sensors 270 are optionally external to a pulse generator yet can provide information to the microcontroller 220.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals and/or other signals across any pair of desired electrodes. The data acquisition system 252 is optionally configured to sense nerve activity and/or muscle activity from muscles other than the heart.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

As already mentioned, the stimulation device 100 can further include or communicate with one or more physiologic sensors 270. The physiologic sensors 270 may be housed within the case 200, on the surface of the case 200 or external to the case 200. The one or more physiologic sensors optionally connect to the device 100 via one or more of the connectors or via other connectors. In some instances, a physiologic sensor may communicate with the microcontroller 220 via a wireless link. For example, a wristwatch physiologic sensor may communicate via electromagnetic radiation signals or other signals with a circuit in the device 100 (e.g., the telemetry circuit 264). Of course, an implantable physiologic sensor may also communicate with the device 100 via such communication means.

A physiologic sensor may be used to implement "rate-responsive" therapy where information sensed is used to adjust pacing stimulation rate according to, for example, the exercise state of the patient. A physiological sensor may be used to sense changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). The microcontroller 220 can respond to such information by adjusting any of the various pacing parameters (e.g., rate, AV Delay, V-V Delay, etc.) or anti-arrhythmia therapy parameters (e.g., timing, energy, leading edge voltage, etc.).

The exemplary device 100 optionally includes a connector capable of connecting a lead that includes a pressure sensor. For example, the connector 221 optionally connects to a pressure sensor capable of receiving information pertaining to chamber pressures or other pressures. Pressures may be related to cardiac performance and/or respiration. Pressure information is optionally processed or analyzed by the upper airway module 239.

Commercially available pressure transducers include those marketed by Millar Instruments (Houston, Tex.) under the mark MIKROTIP®. A study by Shioi et al., "Rapamycin Attenuates Load-Induced Cardiac Hypertrophy in Mice", *Circulation* 2003; 107:1664, measured left ventricular pressures in mice using a Millar pressure transducer inserted through the LV apex and secured in the LV apex with a purse-string suture using 5-0 silk. Various exemplary methods, devices, systems, etc., described herein optionally use such a pressure transducer to measure pressures in the body (e.g., airway, lung, thoracic, chamber of heart, vessel, etc.).

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense pressure, respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device 100 optionally includes circuitry capable of sensing heart sounds and/or vibration associated with events that produce heart sounds. Such circuitry may include an accelerometer as conventionally used for patient position and/or activity determinations. Accelerometers typically include two or three sensors aligned along orthogonal axes. For example, a commercially available micro-electro-mechanical system (MEMS) marketed as the ADXL202 by Analog Devices, Inc. (Norwood, Mass.) has a mass of about 5 grams and a 14 lead CERPAK (approx. 10 mm by 10 mm by 5 mm or a volume of approx. 500 mm$^3$). The ADXL202 MEMS is a dual-axis accelerometer on a single monolithic integrated circuit and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL202 MEMS includes micro-circuitry and a mechanical oscillator.

While an accelerometer may be included in the case of an implantable pulse generator device, alternatively, an accelerometer communicates with such a device via a lead or through electrical signals conducted by body tissue and/or fluid. In the latter instance, the accelerometer may be positioned to advantageously sense vibrations associated with cardiac events. For example, an epicardial accelerometer may have improved signal to noise for cardiac events compared to an accelerometer housed in a case of an implanted pulse generator device.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264. Trigger IEGM storage also can be achieved by magnet.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds (HF indications—pulmonary edema and other factors); detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the ICD device initiates defibrillation therapy.

While an ICD device may reserve defibrillation as a latter tier therapy, it may use defibrillation as a first-tier therapy for VF. In general, an ICD device does not synchronize defibrillation therapy with any given portion of a ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Pathways Associated with Upper Airway Dynamics

Figure 3:
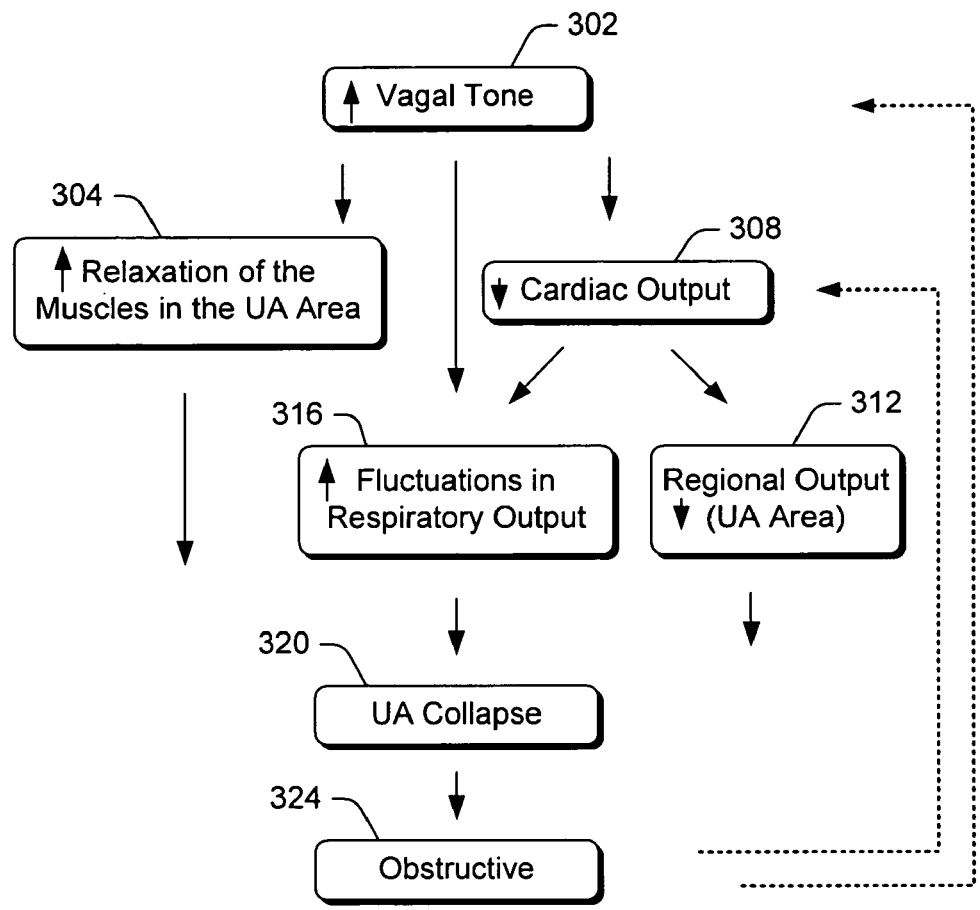
FIG. 3 is a diagram of various pathways related to obstructive apnea.

FIG. 3 shows various pathways and mechanisms 300 related to respiration and in particular upper airway dynamics. As described in more detail with respect to FIG. 4, the muscles of the upper airway act to prevent upper airway collapse during inspiration. As with many muscles of the body, the upper airway muscles are affected by autonomic tone. For example, consider hypervagotonia, which is an elevated vagal tone 302. Hypervagotonia can induce relaxation of the upper airway muscles 304 such that collapse of the upper airway 320 occurs upon contraction of the diaphragm. If upper airway collapse 320 occurs during sleep (e.g., nocturnally), this condition is known as obstructive sleep apnea (OSA) 324.

Where hypervagotonia 302 exists, it can induce bradycardia which results in a lower cardiac output 308. In turn, the lower cardiac output 308 reduces blood flow to region of the upper airway muscles 312 and can cause fluctuations in respiratory output 316. As indicated in FIG. 3, occurrence of obstructive apnea 324 acts to increase hypervagotonia 302. Yet further, obstructive apnea acts to increase the left ventricular transmural pressure. Consequences of such an elevation in transmural pressure include alteration of ventricular filling and reduction in cardiac output. The latter may even cause a shift from obstructive apnea episodes to central apnea episodes. Thus, upper airway dynamics play an important role in cardiac and respiratory performance.

While therapies such as cardiac pacing may address bradycardia induced by hypervagotonia, hypervagotonia may still persist and cause inappropriate relaxation of the upper airway muscles. Various exemplary methods, devices, systems, etc., described herein take appropriate action to maintain sufficient upper airway muscle tone. In turn, such action can prevent or otherwise treat apnea. As described herein, such action may include autonomic nerve stimulation, upper airway muscle stimulation, upper airway nerve stimulation, diaphragm activation (e.g., phrenic nerve stimulation), cardiac stimulation, etc.

While hypervagotonia is mentioned, obstruction of the upper airway can affect sympathetic activity. For example, studies show that activity of the sympathetic nervous system is abnormal in patients with OSA. Sympathetic nervous system activity is elevated during apneic events and peaks at apnea termination in association with the arousal. During obstructive apneas, chemoreflex activation by hypoxemia and hypercapnia causes even further increases in sympathetic activity, with recurrent surges in blood pressure most notable at the end of apneic events. Blood pressure may increase up to 250/130 mm Hg even though the patient is normotensive during wakefulness (see, e.g., Somers et al., "Sympathetic neural mechanisms in obstructive sleep apnea". *J Clin Invest.* 1995; 96:1897-1904).

Patients treated with continuous positive airway pressure (CPAP) after apneic events demonstrate attenuation of the increase in sympathetic nervous system activity while patients with untreated OSA have higher sympathetic nervous system activity compared with controls, even when awake and normoxic. Patients with untreated OSA also have faster heart rates, blunted heart rate variability, and increased blood pressure variability during normoxic daytime wakefulness.

Figure 4:
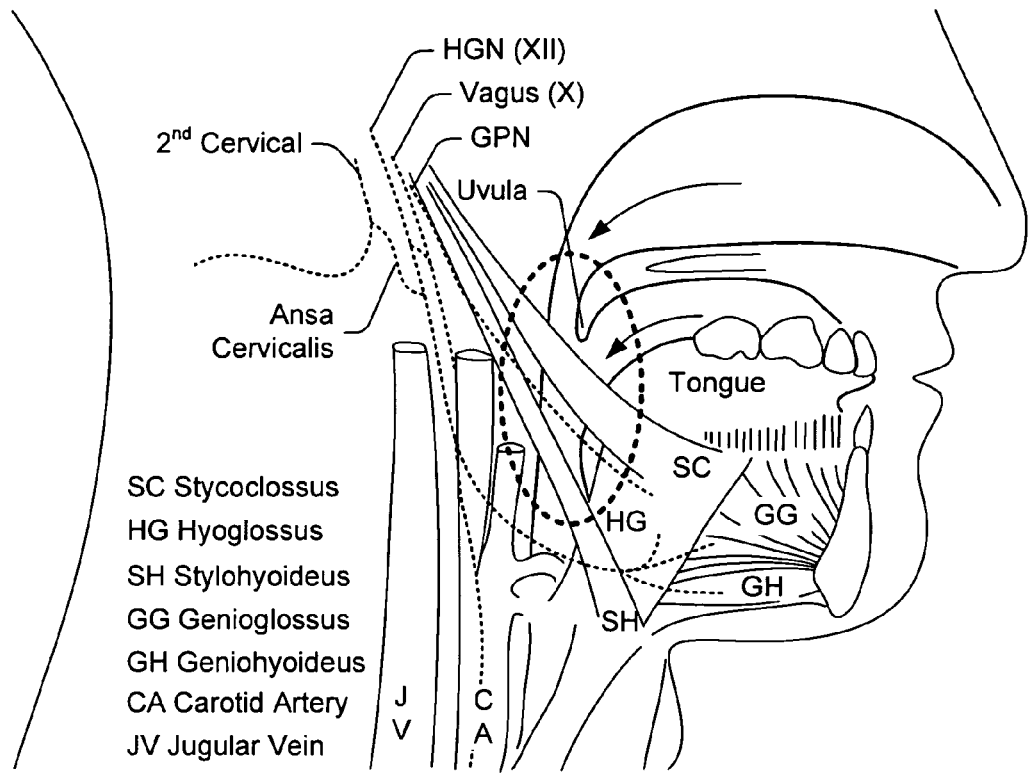
FIG. 4 is a series of anatomical diagrams related to anatomy of the upper airway.
Figure 4:
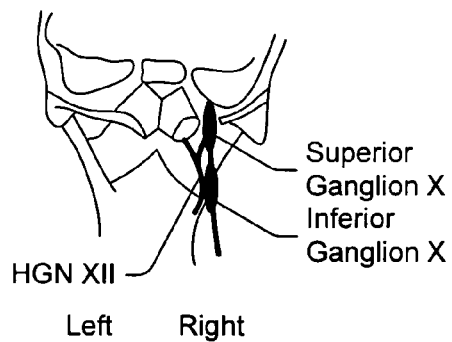
Figure 4:
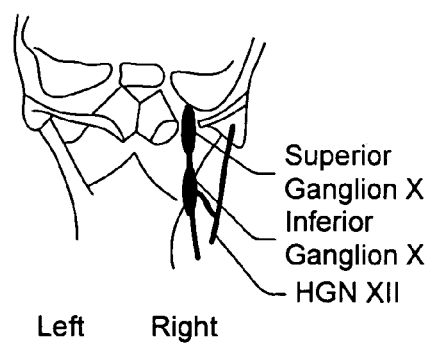

FIG. 4 shows an approximate anatomical diagram of the head and various nerves, muscles, etc., associated with the upper airway. A dashed oval outlines a region whereby the uvula and tongue may obstruct the upper airway. The hypoglossal nerve (HGN; XII) is the motor nerve of the tongue and hence this nerve plays a role in upper airway dynamics. More specifically, the HGN innervates the genioglossus (GG) muscle which has substantial control over the tongue. The GG muscle is the major pharynx dilating muscle and its inspiratory activation is influenced by upper airway mechanoreceptors responsive to negative pressure in the pharynx, chemoreceptors responsive to hypoxia and hyperoxia and by vagal volume related feedback arising from lung inflation. The HGN innervates the GG muscle with both parasympathetic and sympathetic fibers.

The HGN has fibers that arise from the cells of the hypoglossal nucleus. The rootlets of the HGN are collected into two bundles, which perforate the dura mater separately, opposite the hypoglossal canal in the occipital bone, and unite together after their passage through it. The HGN descends almost vertically to a point corresponding with the angle of the mandible. It is at first deeply seated beneath the internal carotid artery and internal jugular vein, and intimately connected with the vagus nerve (X); it then passes forward between the vein and artery, and lower down in the neck becomes superficial below the digastricus. The HGN then loops around the occipital artery, and crosses the external carotid and lingual arteries below the tendon of the digastricus. It passes beneath the tendon of the digastricus, the stylohyoideus (SH), and the mylohyoideus, lying between the last-named muscle and the hyoglossus (HG), and communicates at the anterior border of the HG with the lingual nerve; it is then continued forward in the fibers of the GG muscle as far as the tip of the tongue, distributing branches to its muscular substance.

The HGN has various branches of communication. Communications with the vagus nerve (X) take place close to the skull. Filaments pass between the HGN and the ganglion nodosum of the vagus (X) through the mass of connective tissue which unites the two nerves. A study by Saraswathi, "Communication between the vagus and hypoglossal nerves", *Eur J Anat,* 7(3): 131-134 (2003), reported anatomical results from a study of forty human cadavers. According to this study, in 75% of the cadavers, a connection existed between the vagus and hypoglossal nerves proximal to the inferior ganglion of the vagus and another connection existed from the inferior ganglion itself (see anatomical diagram 410). In 20% of the cadavers there was only one connection joining the inferior ganglion of the vagus with the hypoglossal nerve (see anatomical diagram 420). In 12.5% of the cadavers, the study found that the inferior ganglion of the vagus was bound to the trunk of the hypoglossal nerve and that it was difficult to separate the nerve from the ganglion. The study concluded that the results suggest that the vagal-hypoglossal communication could be the afferent and efferent limbs for reflexes involving the tongue.

Another study (Salame et al., "Surgical anatomy of the cervical segment of the hypoglossal nerve", *Clin Anat.* 2006 January; 19(1): 37-43) reported various communications between the extracranial HGN and other nerves. In particular, the study of Salame et al. reported communication between the HGN (XII) and the inferior ganglion of the vagus (X) in all cadavers and additional communications with the vagus (X) in 11% of the cadavers. With respect to sympathetic communications, 46% of the cadavers included communications between the HGN (XII) and the sympathetic trunk at the level of the superior cervical ganglion. Communications were also found between the HGN (XII) and the ansa hypoglossi (7% of cadavers), the lingual nerve (24% of cadavers) and the spinal accessory nerve (2% of the cadavers). The study of Salame et al. also reported that it is feasible to split the fibers of the HGN (XII) longitudinally and to use only part of them for reanimation of other nerves, while leaving the other part for innervation of the ipsilateral tongue muscles (the average diameter of the HGN was reported to be about 3 mm). As described herein, splitting of the fibers may be performed to enhance selectivity of sensing activity and/or stimulating fibers of the HGN (XII).

As the HGN winds around the occipital artery it gives off a filament to the pharyngeal plexus (see also, e.g., glossalpharyngeal nerve (GPN)). Communication with sympathetic nerves takes place opposite the atlas by branches derived from the superior cervical ganglion, and in the same situation HGN (XII) is joined by a filament (ansa cervicalis) derived from the loop connecting the first and second cervical nerves. Communications with the lingual nerve take place near the anterior border of the HG muscle by numerous filaments which ascend upon the muscle.

Muscular branches of the HGN (XII) are distributed to the SG muscle, HG muscle, geniohyoideus (GH) muscle and GG muscle. At the under surface of the tongue numerous slender branches pass upward into the substance of the organ to supply its intrinsic muscles.

Overall, maintenance of upper airway patency ultimately depends on a balance between stabilizing and collapsing forces. Factors involved in effective stabilization of upper airway structures include upper airway neuromuscular activity, physiological properties of upper airway muscles, effectiveness of upper airway muscle contraction and mechanical coupling of upper airway muscles to surrounding soft tissues.

Phasic activity of upper airway muscles is known to precede that of respiratory muscles in normal patients as well as those affected by OSA. The contraction of upper airway dilators generates the only stabilizing force that opposes a series of collapsing forces, including the effects of gravity-induced posterior displacement of upper airway structures, the negative inspiratory upper airway transmural pressure gradient, and surface tension forces. Maintenance or alteration of upper airway patency may consider contraction of dilators as well as characteristics of the collapsing forces.

As described herein, sensing of nerve activity, sensing of muscle activity, delivery of energy to one or more nerves and/or delivery of energy to one or more muscles may be used to maintain upper airway patency. For example, delivery of energy to block parasympathetic activity may increase tone of one or more upper airway muscles and thereby prevent the tongue from obstructing the upper airway. Alternatively, or in addition to this example, delivery of energy to increase sympathetic activity may increase tone of one or more upper airway muscles and thereby prevent the tongue from obstructing the upper airway.

Figure 5:
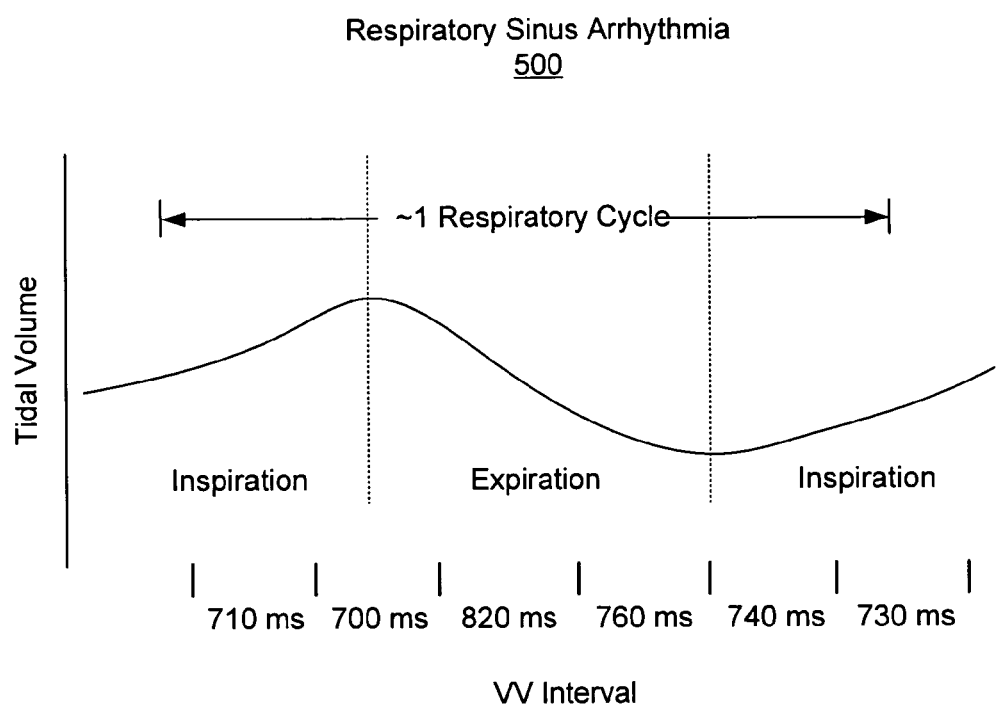
FIG. 5 is a plot of tidal volume and R-wave incidence versus time for about 1 respiratory cycle.

FIG. 5 shows a plot 500 of tidal volume and RR interval to illustrate respiratory sinus arrhythmia (RSA). RSA is a natural cycle of arrhythmia that occurs through the influence of breathing on autonomic tone. During inspiration vagus nerve activity is impeded, which shifts the autonomic tone towards sympathetic. In response, the RR interval shortens, i.e., heart rate increases. During expiration, the autonomic tone shifts toward parasympathetic and the RR interval lengthens, i.e., heart rate decreases. While research indicates that both parasympathetic and sympathetic mechanisms contribute to RSA, RSA is primarily due to changes in parasympathetic activity.

As described herein, sensing heart rate or RR interval may be used to determine one or more respiratory characteristics. For example, if heart rate does not change over a period of about 3 to about 10 cardiac cycles, then the patient may be entering or experiencing apnea. Further, sensing heart rate or RR interval may be used in conjunction with a measure of respiration to estimate autonomic tone or other autonomic characteristic. For example, if there is little change in heart rate over one or more respiratory cycles, then the autonomic tone may be shifted toward sympathetic. Yet further, excessive RSA may indicate an overactive parasympathetic system.

Various Exemplary Methods

Figure 6:
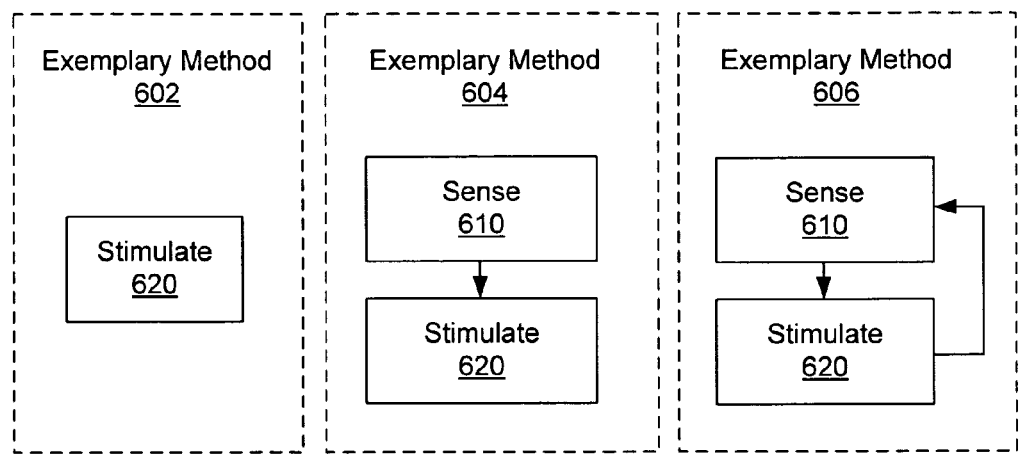
FIG. 6 is a block diagram of various exemplary methods and exemplary actions.
Figure 6:
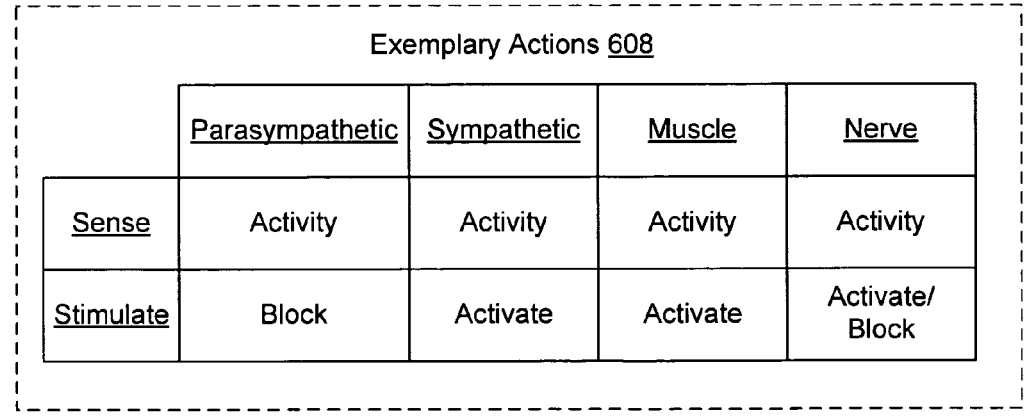

FIG. 6 shows various exemplary methods for altering or maintaining upper airway patency 600. An exemplary method 602 includes a stimulation block 620 that stimulates an autonomic nerve, other nerve and/or muscle to alter or maintain upper airway patency. For example, consider the anatomical diagram 420 of FIG. 4 where a connection exists between the HGN (XII) and the vagus (X). The exemplary method 602 may rely on delivery of stimulation energy via one or more electrodes positioned proximate to the connection to thereby block efferent parasympathetic traffic or activity to the genioglossus muscle. In turn, the autonomic tone of the genioglossus muscle is shifted toward sympathetic and the muscle tone increased to promote upper airway patency. Such a method may operate on the left side, the right side or both sides. Similarly, such a method may be adjusted appropriately depending on patient anatomy. For example, consider the anatomical diagram 410 of FIG. 4 where a method may rely on delivery of stimulation energy via one or more electrodes positioned proximate to the connection proximal to the inferior ganglion of the vagus (X). An exemplary method may aim to block activity in such a connection without substantially altering activity of the vagus (X).

As already mentioned, the HGN (XII) may be split longitudinally in the extracranial region. After splitting, one or more electrodes may be positioned to stimulate certain fibers. Feedback may be used to determine which fibers are directed to muscles responsible for upper airway patency. Once such a fiber or fibers have been identified, then the exemplary method 602 may delivery energy to one or more electrodes to stimulate the identified fiber or fibers. In this example, the energy may be sufficient to activate the identified HGN fiber or fibers and thereby cause contraction of one or more muscles responsible for upper airway patency.

The exemplary method 602 optionally delivers energy via one or more electrodes whereby the energy level is below a muscle stimulation threshold. Such subthreshold delivery aims to alter muscle and/or autonomic tone without directly causing muscle activation (e.g., genioglossus or other muscle(s)).

Various exemplary methods may rely on a cuff electrode(s) to deliver energy to a nerve. Further, such a cuff electrode or electrodes may be used for sensing electrical activity. Various exemplary methods may rely on an electrode array whereby all electrodes of the array or one or more selected electrodes of the array may be used to delivery energy or to sense electrical activity.

An exemplary method 604 includes a sense block 610 and a stimulate block 620. The sense block 610 may perform any of a variety of sensing such as, but not limited to, sensing parasympathetic activity, sensing sympathetic activity, sensing muscle activity and sensing motor nerve activity. Sensing may rely on one or more electrodes to sense electrical activity. Sensing may sense impedance such as intrathoracic impedance and thereby determine respiratory characteristics.

In the method 604, the stimulate block 620 delivers stimulation based at least in part on information obtained by the sense block 610. For example, if the sense block 610 senses an increase in efferent parasympathetic activity to the genioglossus muscle, then the stimulate block 620 may call for delivery of stimulation energy to impede this activity and thereby enhance tone of the genioglossus muscle to maintain upper airway patency.

An exemplary method 606 includes features of the method 604 and a feedback loop between a sense block 610 and a stimulate block 620. The method 606 may implement a learning algorithm to adjust sensing and/or stimulation based at least in part on feedback. For example, consider a method that includes sensing autonomic nerve activity and stimulating to block parasympathetic activity and/or stimulating to increase sympathetic activity. If the stimulating does not sufficiently alter the autonomic nerve activity, per sensing, then one or more parameters of the stimulating may be adjusted to achieve a more desirable result.

Various possible sensing and stimulation sites may be selected with reference to the discussion of FIG. 4 and the studies of Salame et al. and Saraswathi. Other sensing and/or stimulation may be used in conjunction with the exemplary methods 602, 604, 606. For example, thoracic or intrathoracic impedance may be used to sense respiration. Sensing may include acquisition of cardiac electrograms (surface, intrathoracic, etc.). Photoplethysmography may be used for a variety of purposes, for example, sensing blood gas levels. In turn, blood gas levels may be used to determine characteristics of respiration.

Figure 7:
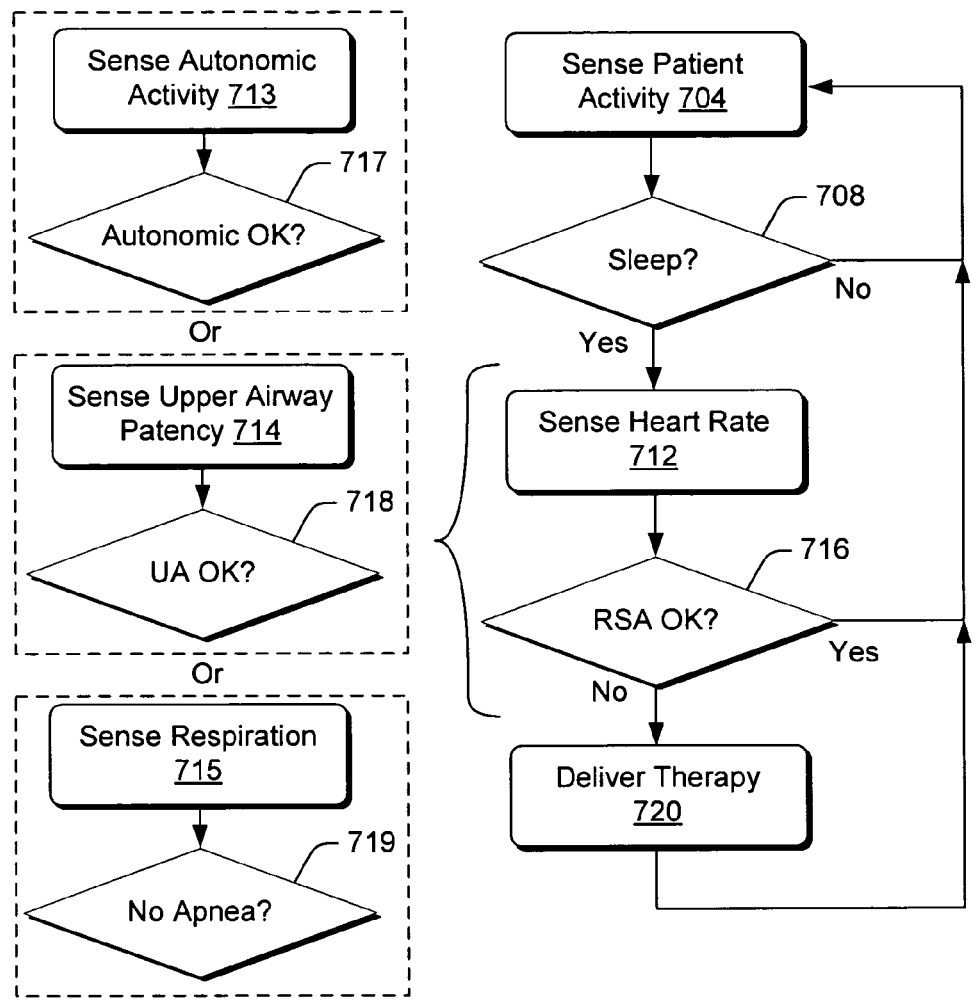
FIG. 7 is a block diagram of an exemplary method and various alternative or complementary actions.

FIG. 7 shows an exemplary method 700 for maintaining or altering upper airway patency. The method 700 commences in a sense block 704 that senses patient activity. The sense block 704 may rely on any of a variety of techniques to sense patient activity such as accelerometers, heart rate and other physiological measures. Alternatively, or in addition to, a timer or clock may be used to infer patient activity (e.g., sleeping hours, etc.). A decision block 708 follows that decides if the patient is sleeping. If the patient is not sleeping, then the method 700 continues in the sense block 704.

If the decision block 708 decides that the patient is sleeping, then the method 700 continues in another sense block 712 that senses heart rate. In this example, heart rate is monitored for evidence of respiratory sinus arrhythmia (RSA). A decision block 716 follows that decides if RSA is OK, i.e., indicative or normal respiration and/or normal autonomic tone. If the decision block 716 decides that RSA is OK, then the method 700 continues, for example, in the sense block 704. However, if RSA is not OK per the decision block 716, then the method 700 continues in a delivery block 720 that calls for delivery of therapy. For example, a lack of RSA may indicate obstructive apnea or excessive RSA may indicate a change in autonomic tone associated with an increase in parasympathetic activity that may compromise upper airway patency. In response, the therapy block 720 delivers a therapy to maintain or increase upper airway patency.

As shown in FIG. 7, alternatives exist for the sense block 712 and the decision block 716. For example, in one alternative, a sense autonomic activity block 713 senses autonomic activity using one or more electrodes positioned proximate to an autonomic pathway and a decision block 717 decides if the autonomic activity is OK or indicative of compromised upper airway patency.

In another alternative, a sense upper airway patency block 714 senses or determines upper airway patency using any of a variety of techniques (e.g., sensing muscle activity, sensing intrathoracic impedance, etc.). A decision block 718 decides if the upper airway patency is OK or indicative of compromised upper airway patency.

In yet another alternative, a sense respiration block 715 senses respiration and a decision block 719 decides if apnea exists. A further decision may be made as to whether apnea is central or obstructive. For the case of obstructive apnea, the therapy block 720 delivers therapy to increase upper airway patency.

An exemplary method optionally uses more than one of the decision blocks 716, 717, 718, 719. For example, a method may cascade the various blocks or implement control logic in the form of a decision tree. An exemplary method may tailor the various blocks according to patient condition or other criteria.

Exemplary Upper Airway Device

Figure 8:
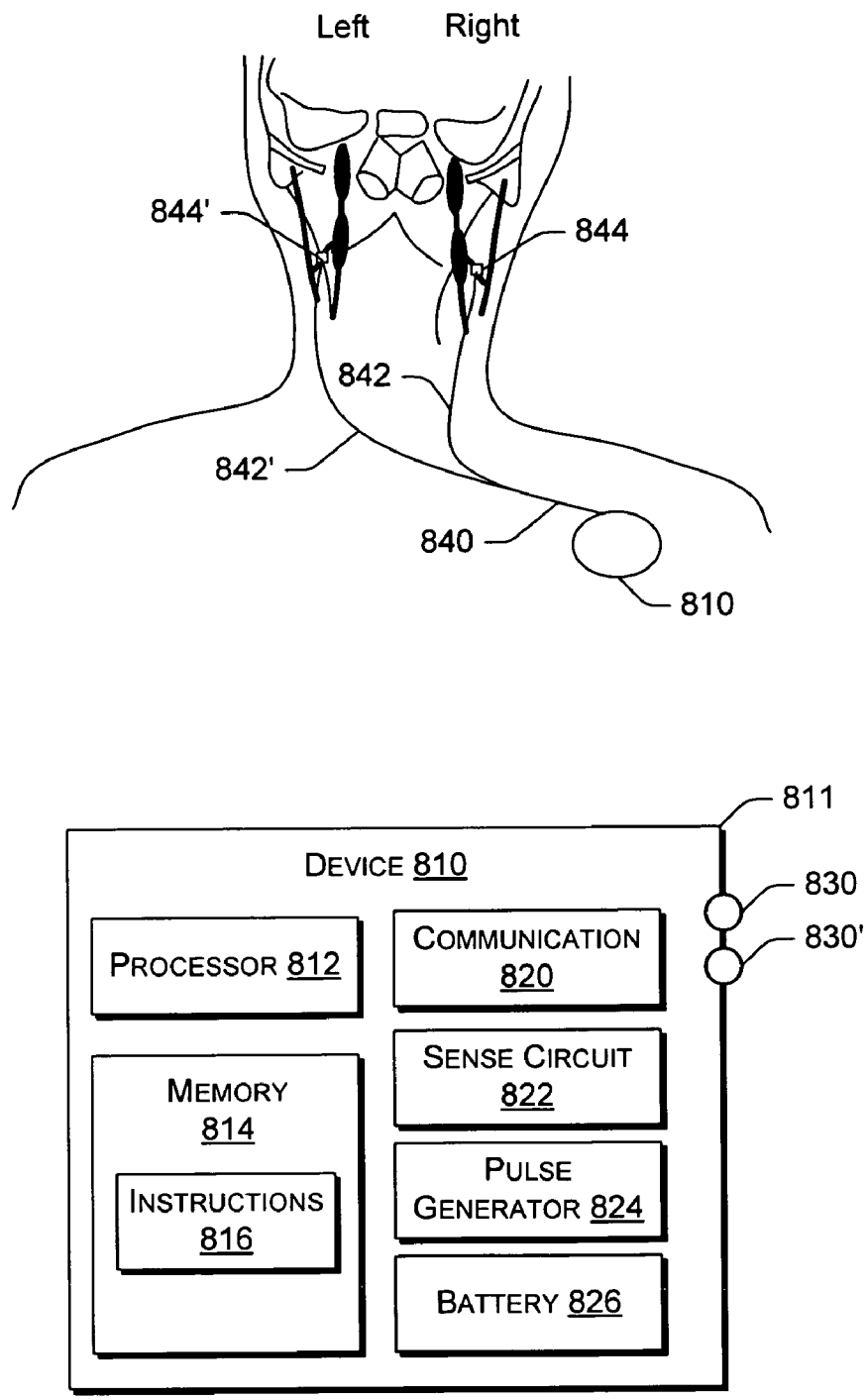
FIG. 8 is a diagram of an exemplary device implanted in a patient that includes one or more electrodes for sensing and/or stimulating a nerve associated with upper airway patency.

FIG. 8 shows an exemplary device 810 for maintaining or altering upper airway patency. In this example, the device includes a bifurcated lead 840 having bifurcations 842, 842'. Each bifurcation includes one or more electrodes 844, 844'. In this example, at least one electrode is positioned to delivery energy and/or to sense activity in a connection between the vagus (X) and the HGN (XII). More specifically, at least one electrode 844 is positioned between the right vagus and the right HGN and at least one electrode 844' is positioned between the left vagus and the left HGN. Alternative examples may include one or more electrodes positioned to sense or to stimulate the HGN, a sympathetic nerve associated with the HGN, etc. A combination of such arrangements is also possible.

The exemplary device 810 may be an implantable device and include any of a variety of features of the device 100 of FIGS. 1 and 2. As shown in the example of FIG. 8, the device 810 includes a processor and memory 814 that can store instructions 816. Execution of the instructions 816 by the processor 812 can cause the device 810 to perform various operations (see, e.g., the various exemplary methods described herein).

The device 810 includes communications circuit 820, a sense circuit 822, a pulse generator 824 and a battery 826 or other power source capable of powering the device 810. The device 810 includes one or more connectors 830, 830'. A lead such as the lead 840 may be connected to the device 810 via the one or more connectors 830, 830'.

The device 810 may further include features for cardiac therapy, diaphragm activation, etc. The device 810 may be implanted in a pectoral pocket or other location. The device 810 is optionally configured to be fitted to the skull of a patient. For example, consider a cochlear implant, which is surgically implanted under the skin behind the ear.

An exemplary device includes a processor, a lead bearing one or more electrodes positionable proximate to an autonomic pathway and control logic, operable in conjunction with the processor, to call for delivery of energy via the one or more electrodes to alter autonomic tone of the geniglossus muscle. Such a device may include control logic to call for acquisition of respiratory information and the device may call for delivery of energy based at least in part on the respiratory information.

An exemplary device may include control logic to call for acquisition of heart rate where, for example, control logic may determine one or more respiratory characteristics based at least in part on heart rate (e.g., respiratory sinus arrhythmia, etc.). Such control logic may allow for diagnosis of apnea or risk of apnea and, in turn, call for a therapy that aims to increase upper airway patency by altering autonomic tone.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method to prevent or alleviate obstructive apnea comprising:
   sensing respiration;
   sensing a decrease in a change in heart rate over a predetermined number of cardiac cycles; and
   based at least in part on the sensing respiration and sensing a decrease in a change in heart rate over the predetermined number of cardiac cycles, deciding whether to deliver energy to one or more electrodes positioned proximate to an autonomic pathway to alter autonomic tone of the geniglossus muscle.

2. The method of claim 1 further comprising sensing autonomic nerve activity.

3. The method of claim 1 wherein the sensing respiration comprises sensing impedance.

4. The method of claim 1 wherein the deciding decides to increase sympathetic activity.

5. The method of claim 1 wherein the deciding decides to decrease parasympathetic activity.

6. The method of claim 1 further comprising sensing autonomic nerve activity after or during delivery of energy to the one or more electrodes.

7. The method of claim 1 wherein if the deciding decides to delivery energy, the delivery of energy occurs during inspiration.

8. The method of claim 1 wherein if the deciding decides to delivery energy, the delivery of energy occurs during a ventricular refractory period.

9. The method of claim 1 further comprising delivering energy to one or more electrodes to pace the heart.

10. The method of claim 1 wherein the sensing respiration comprises sensing phrenic nerve activity.

11. The method of claim 1 wherein the sensing respiration comprises sensing diaphragmatic activity.

12. The method of claim 1 wherein the predetermined number of cardiac cycles is about 3 to about 10 cardiac cycles.

13. A system to prevent or alleviate obstructive apnea comprising:
   a lead bearing one or more electrodes positionable to deliver energy to a neural pathway between a vagus nerve and a hypoglossal nerve; and
   control logic adapted to be coupled to the lead and operative to sense respiration and sense a decrease in a change in heart rate over a predetermined number of cardiac cycles and, based on the sensing respiration and the sensing a decrease in a change in heart rate over the predetermined number of cardiac cycles, to call for delivery of energy to the neural pathway via the lead.

14. The system of claim 13 wherein the one or more electrodes allow for sensing nerve activity in a neural pathway between a vagus nerve and a hypoglossal nerve.

15. The system of claim 13 wherein the lead comprises one or more electrodes positionable to deliver energy to a neural pathway between the right vagus nerve and the right hypoglossal nerve.

16. The system of claim 13 wherein the lead comprises one or more electrodes positionable to deliver energy to a neural pathway between the left vagus nerve and the left hypoglossal nerve.

17. The system of claim 13 wherein the predetermined number of cardiac cycles is about 3 to about 10 cardiac cycles.

18. A system to prevent or alleviate obstructive apnea comprising:

means for sensing respiration;

means for sensing a decrease in a change in heart rate over a predetermined number of cardiac cycles; and means for deciding, based at least in part on the sensing respiration and sensing a decrease in a change in heart rate over the predetermined number of cardiac cycles, whether to deliver energy to one or more electrodes positioned proximate to an autonomic pathway to alter autonomic tone of the geniglossus muscle.

19. The system of claim 18 further comprising means for sensing autonomic nerve activity.

20. The system of claim 18 wherein the means for sensing respiration comprises means for sensing impedance.

21. The system of claim 18 wherein the means for deciding comprises means for increasing sympathetic activity.

22. The system of claim 18 wherein the predetermined number of cardiac cycles is about 3 to about 10 cardiac cycles.

* * * * *

UNITED STATES PATENT AND TRADEMARK OFFICE
CERTIFICATE OF CORRECTION

| | | |
|---|---|---|
| PATENT NO. | : 7,650,189 B1 | Page 1 of 1 |
| APPLICATION NO. | : 11/446179 | |
| DATED | : January 19, 2010 | |
| INVENTOR(S) | : Park et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 504 days.

Signed and Sealed this

Twenty-third Day of November, 2010

David J. Kappos
*Director of the United States Patent and Trademark Office*